(12) United States Patent
Lee et al.

(10) Patent No.: US 11,131,454 B2
(45) Date of Patent: Sep. 28, 2021

(54) MICRO-LIGHT EMITTING DEVICE ARRAY CONTACTING SKIN, METHOD FOR FABRICATING THE SAME, AND CHARGING SYSTEM FOR LIVING-BODY IMPLANTABLE ELECTRONIC DEVICE

(71) Applicant: GWANGJU INSTITUTE OF SCIENCE AND TECHNOLOGY, Gwangju (KR)

(72) Inventors: Jongho Lee, Gwangju (KR); Juho Kim, Gwangju (KR)

(73) Assignee: Gwangju Institute of Science and Technology, Gwangju (KR)

( * ) Notice: Subject to any disclaimer, the term of this patent is extended or adjusted under 35 U.S.C. 154(b) by 0 days.

(21) Appl. No.: 17/066,342

(22) Filed: Oct. 8, 2020

(65) Prior Publication Data

US 2021/0108793 A1 Apr. 15, 2021

Related U.S. Application Data

(60) Provisional application No. 62/915,157, filed on Oct. 15, 2019.

(51) Int. Cl.
*F21V 33/00* (2006.01)
*F21V 29/70* (2015.01)
(Continued)

(52) U.S. Cl.
CPC ........ *F21V 33/0068* (2013.01); *A61N 1/3787* (2013.01); *A61N 5/1029* (2013.01);
(Continued)

(58) Field of Classification Search
CPC ...... F21V 29/70; F21V 29/89; F21V 33/0068; F21V 21/0808; A61N 5/06–0603;
(Continued)

(56) References Cited

U.S. PATENT DOCUMENTS

| 6,096,066 A * | 8/2000 | Chen ................ A61N 5/062 |
| | | 607/88 |
| 10,441,185 B2 * | 10/2019 | Rogers ............... A61N 1/0472 |
| 10,653,890 B2 * | 5/2020 | Iguchi ................ A61N 5/0616 |

FOREIGN PATENT DOCUMENTS

| FR | 3034022 A1 * | 9/2016 | ........... A61N 5/0616 |
| FR | 3034167 A1 * | 9/2016 | ........... A61N 5/0616 |

(Continued)

OTHER PUBLICATIONS

Bereuter et al. "Energy Harvesting by Subcutaneous Solar Cells: A Long-Term Study on Achievable Energy Output." Annals of Biomedical Engineering, vol. 45, No. 5 (May 2017).

*Primary Examiner* — Mariceli Santiago
(74) *Attorney, Agent, or Firm* — Loza & Loza, LLP; Heidi Eisenhut (57) ABSTRACT

A light emitting device array includes a substrate, a heat sink disposed on the substrate, at least two light emitting devices disposed on the heat sink and spaced apart from each other, a connector disposed on the light emitting device and configured to apply power, an insulating layer interposed between the heat sink and the connector, a fixing member configured to support a position of the light emitting device, on the light emitting device, and an adhesive layer provided on the fixing member to make contact with a skin.

15 Claims, 10 Drawing Sheets

(51) Int. Cl.
    *F21V 29/89*     (2015.01)
    *F21K 9/90*      (2016.01)
    *A61N 1/378*     (2006.01)
    *A61N 5/10*      (2006.01)
    *F21V 21/08*     (2006.01)
    *A61N 1/375*     (2006.01)
    *F21Y 115/10*    (2016.01)

(52) U.S. Cl.
    CPC ............ *F21K 9/90* (2013.01); *F21V 21/0808* (2013.01); *F21V 29/70* (2015.01); *F21V 29/89* (2015.01); *A61N 1/37512* (2017.08); *F21Y 2115/10* (2016.08)

(58) Field of Classification Search
    CPC ...... A61N 5/0616–0625; A61N 5/1029; A61N 1/3787
    See application file for complete search history.

(56) References Cited

FOREIGN PATENT DOCUMENTS

| | | | |
|---|---|---|---|
| KR | 20170138806 A | * | 12/2017 |
| KR | 101913774 B1 | * | 10/2018 |
| KR | 102067101 B1 | * | 1/2020 |
| WO | WO-2020242141 A1 | * | 12/2020 ............... A61N 5/06 |

* cited by examiner

No heat sink

FIG. 10A

Narrow and thin

FIG. 10B

Wide and thin(2μm)

FIG. 10C

Wide and thick(5μm)

MICRO-LIGHT EMITTING DEVICE ARRAY CONTACTING SKIN, METHOD FOR FABRICATING THE SAME, AND CHARGING SYSTEM FOR LIVING-BODY IMPLANTABLE ELECTRONIC DEVICE

CROSS-REFERENCE TO RELATED APPLICATIONS

This application claims priority under 35 U.S.C. § 119 to U.S. Provisional Patent Application No. 62/915,157 filed on Oct. 15, 2019, the entire contents of which is hereby incorporated by reference in its entirety.

BACKGROUND

The present disclosure relates to a micro-light emitting device.

With the development of technologies, many devices implantable (hereinafter, briefly referred to as "electronic device" instead of an implantable device) into a living body have been introduced. The electronic device may operate only when receiving power. In general, the electronic device may receive power by replacing a battery thereof with new one. When a patient suffers an operation to replace the battery with new one, the patient may be burdened. There has been suggested a manner of charging the battery from the outside to solve the above problem.

Cited reference 1 demonstrates an amount of ambient light energy supplied from the outside to an electronic device provided under a skin. As recognized from cited reference 1, when the electronic device receives the energy using the ambient light, a small amount of energy is charged. Inside a body, since a receive terminal to receive energy, an electronic device to perform a biological action, and an operating position of the electronic device are variable, a long electric wire is necessary. The electric wire may cause a side effect to a human body.

PRIOR ART

Non-Patent Document

L. Bereuter, et al., Energy Harvesting by Subcutaneous Solar Cells: A Long-Term Study on Achievable Energy Output. Ann. Biomed. Eng. 45, 1172-1180 (2017).

SUMMARY

The present disclosure is to provide a micro-light emitting array capable of intensively transmitting energy to an electronic device implantable into a living body.

The present disclosure is to provide a micro-light emitting array capable of directly transmitting a large amount of energy by making contact with a skin.

According to an aspect of the present disclosure, a light emitting device array may include a substrate, a heat sink disposed on the substrate, at least two light emitting devices disposed on the heat sink and spaced apart from each other, a connector disposed on the light emitting device to apply power, an insulating layer interposed between the heat sink and the connector, a fixing member to support a position of the light emitting device, on the light emitting device, and an adhesive layer provided on the fixing member to make contact with a skin.

The light emitting device array may have a through hole vertically formed through the light emitting device array. The inner part of the through hole may be empty.

The light emitting device array may include through holes formed at least two of the substrate, the heat sink, the connector, the insulating layer, or the adhesive layer.

The through holes may be vertically aligned.

The through holes may be provided in all the substrate, the heat sink, the connector, the insulating layer, and the adhesive layer The heat sink may include multi-metal layers.

A lowermost part of the multi-metal layers may include copper (Cu).

The heat sink and the light emitting device may directly make contact with each other.

Power may be applied to the heat sink such that the light emitting device receives the power.

The light emitting device may receive power applied through the connector.

At least one of the heat sink and the connector may have a pattern formed by repeating a cell serving as an area in which one light emitting device is disposed At least one of the heat sink and the connector may have an interconnector to connect a pair of cells adjacent to each other.

A through hole may be provided in at least one of opposite side surfaces of the interconnector to allow air to flow through the through hole.

The interconnector may protrude from each side of the cell. The interconnector may more protrude outward from the side of the cell.

The interconnector may have a length that extends in a longitudinal direction to link adjacent cells to each other, and is greater than a length extending in a thickness direction perpendicular to the longitudinal direction.

According to another aspect of the present disclosure, a method for fabricating a light emitting device array may include providing a light emitting device on a sacrificial substrate, moving the light emitting device to a stamping substrate and seating the resultant structure on a heat sink, removing the stamping substrate such that the heat sink and the light emitting device remain, providing an insulating layer on the light emitting device, providing a connector on the insulating layer, providing a fixing member to fix the light emitting device after providing the connector, and providing an adhesive layer, which makes contact with a skin, onto the fixing member.

The adhesive layer may be provided through a screen printing scheme and a cooling air injection scheme.

The light emitting device on the sacrificial substrate may be covered with a protective member.

The protective member may be removed with acetone in a process of removing the stamping substrate The light emitting device and the heat sink may be cold welded.

According to another aspect of the present disclosure, a charging system for an electronic device implantable into a living body may include a living-body implantable electronic device inserted into a skin and having a secondary battery, and a light emitting array to make contact with the skin.

The light emitting array may include a heat sink, at least two light emitting devices disposed on the heat sink and spaced apart from each other, a connector disposed on the light emitting device, an insulating layer disposed on an interface between the heat sink and the connector, and an adhesive layer provided on the connector to make contact with the skin.

The charging system may have a through hole vertically formed through the light emitting device array and having an inner part that is empty.

At least one of the heat sink and the connector may apply power to the light emitting device.

According to the present disclosure, there may be provided the light emitting array to make contact with the skin. Energy may be easily and rapidly supplied to the living body using the electronic device.

DETAILED DESCRIPTION OF THE EMBODIMENTS

Hereinafter, the detailed embodiment of the present disclosure will be described with reference to accompanying drawings. The spirit of the present disclosure is not limited to suggested embodiments, and those skilled in the art, which understand the spirit of the present disclosure, may easily suggest another embodiment by adding, modifying, and deleting components within the same technical scope.

Figure 1:
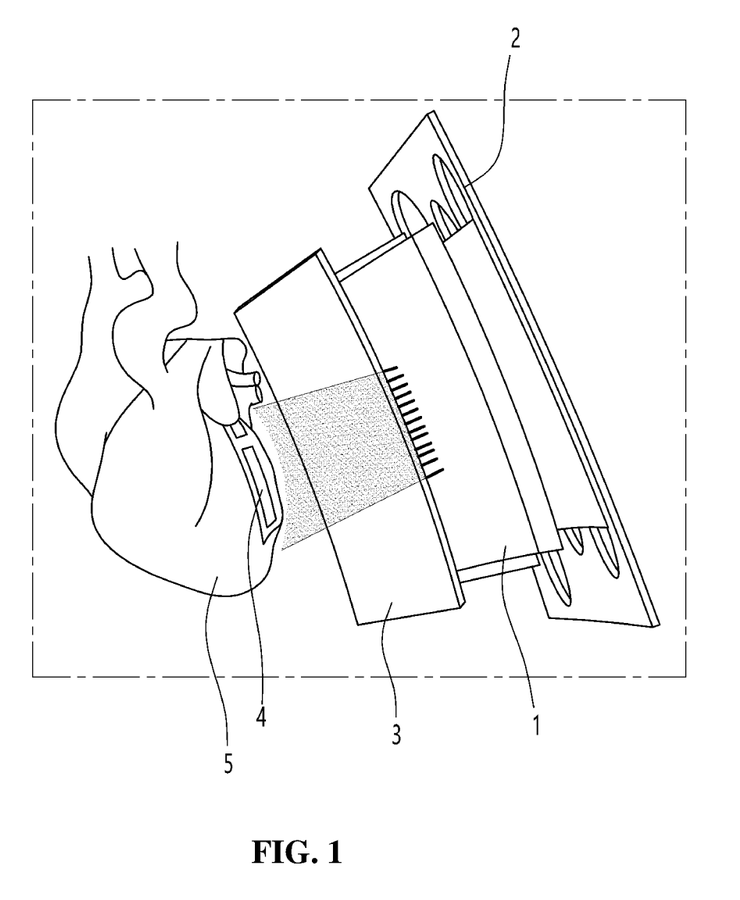
FIG. 1 is a view illustrating the use of a light emitting device array, according to an embodiment.

FIG. 1 is a view illustrating the use of a light emitting device array, according to an embodiment.

Referring to FIG. 1, in a light emitting device array 1 according to an embodiment, a plurality of light emitting devices may be provided in the form of an array. The light emitting device may be a micro-light emitting diode. The light emitting device may adhere to a skin 3 of a living body. The light emitting device may make contact with the skin of the living body. A living-body implantable electronic device (hereinafter, briefly referred to as "electronic device") 4 may be implanted into the skin. The electronic device may be a pacemaker by way of example. The pacemaker may aid the biological action of an organ 5 exemplified as the heart. The electronic device may have a secondary battery. The secondary battery may wirelessly receive energy from the light emitting device array 1.

A sheath 2 may be placed outside the light emitting device array 1. The sheath 2 may be an example of cloth worn by a user. The light emitting device array 1 may be placed in cloth. Indirect lighting provided outside the cloth may be blocked by the cloth except for direct lighting by the light emitting device array 1. The indirect lighting may not actually supply energy to the secondary battery. The actually received energy by the secondary battery may be all energy provided by the light emitting device array 1.

Figure 2:
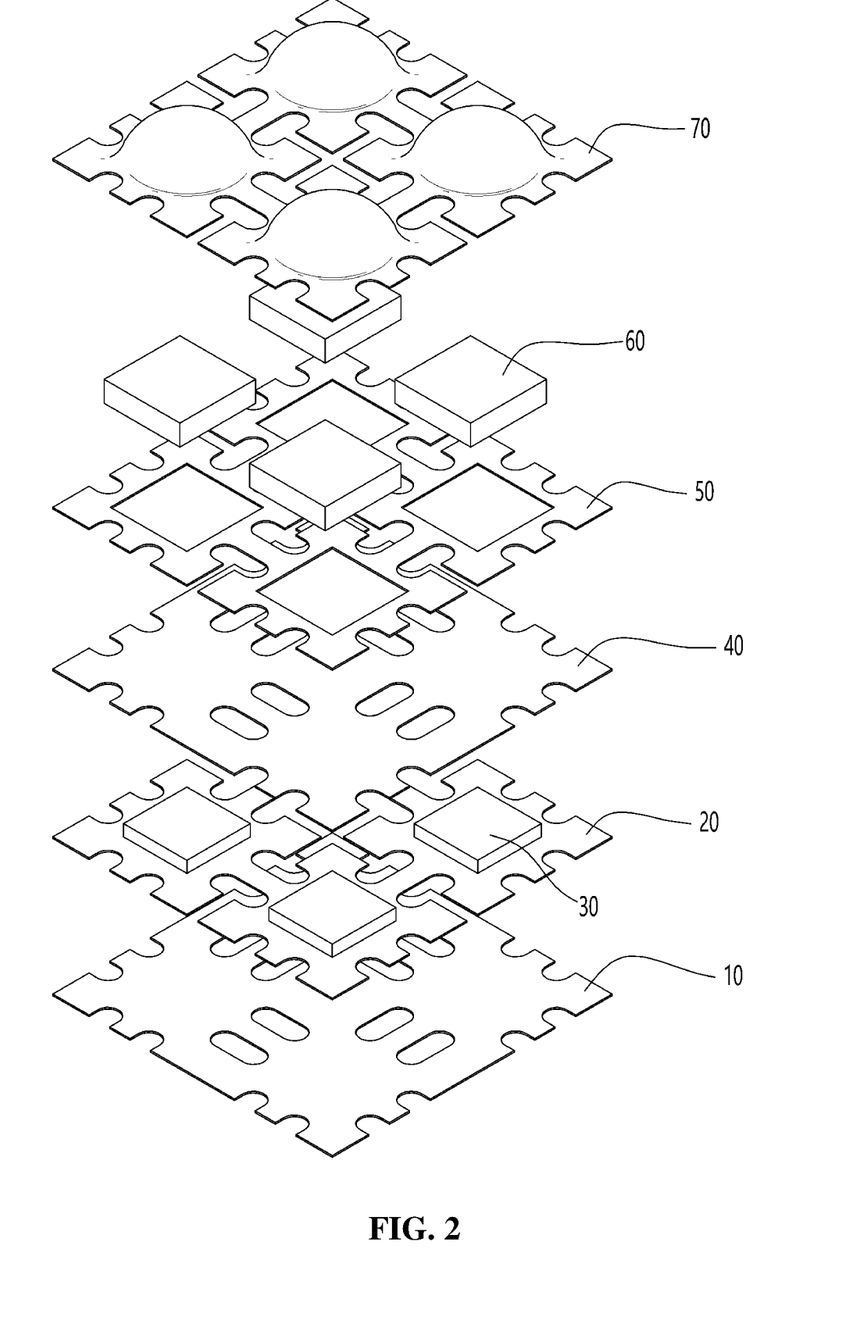
FIG. 2 is an exploded perspective view illustrating the light emitting device array.

FIG. 2 is a schematic exploded perspective view illustrating the light emitting device array.

Referring to FIG. 2, a substrate 10 may be provided at the lowermost portion. The substrate may include a polyimide (PI) substrate.

A heat sink 20 may be provided on the substrate 10. The heat sink 20 has a configuration of (Au/Ni/Ti/Cu=150 nm/10 nm/200 nm/5 μm), and may be stacked upward starting with copper in contact with the substrate. Thermal diffusion may be promoted through the configuration.

At least two light emitting devices 30 are spaced apart from each other by a specific distance on the heat sink 20 while directly making contact with the heat sink 20. The light emitting device may be a micro-light emitting device (LED) of micro-light emitting device AlGaInP series and may emit infrared rays. Each size of the light emitting device is 250*250 square μm2, and the thickness of the light emitting device may reach 4.1 μm.

The light emitting device 30 may be directly coupled to the heat sink 20. The light emitting device and the heat sink may make contact with each other through cold welding. Since the light emitting device and the heat sink make contact with two surfaces in a large area, contact resistance may be reduced. Heat generated from the contact surface between the light emitting device and the heat sink may be reduced. The heat from the light emitting device may be smoothly radiated to the heat sink through the large contact area between the light emitting device and the heat sink.

An insulating layer 40 is stacked on the light emitting device 30 and the heat sink 20. The insulating layer may use an "SU-8" insulating layer. The insulating layer 40 may have 2 μm. The insulating layer 40 may insulate the heat sink 20 from a connector 50.

The connector 50 may be provided on the insulating layer 40. The connector supplies energy, in contact with an upper portion of the light emitting device 30. The connector may be provided with Ni 100 nm/Au 200 nm.

The connector 50 may be a second electrode layer. The heat sink 20 may be a first electrode layer. The second electrode layer and the first electrode layer may extend horizontally, and each may be provided as a single body. The first electrode layer is conducted with the light emitting device under the light emitting device, when viewed from FIG. 2. The second electrode layer is conducted with the light emitting device above the light emitting device, when viewed from FIG. 2. The first electrode layer and the second electrode layer may supply energy to all light emitting devices. The first electrode layer and the second electrode layer may receive power having mutually different polarities.

A fixing member 60 may be placed on the connector 50. The fixing member 60 may physically fix the position of the light emitting device 30. The fixing member 60 may be formed of Norland Optical Adhesive 61 ("NOA 61"). The fixing member 60 may be provided with the thickness of 20 μm in the size of 270*270 μm2.

An adhesive layer 70 may be provided on the fixing member 60. The adhesive layer may be formed of Silbione RT Gel 4717 A/B or Bluestar Silicone.

The light emitting device array 1 may have a through hole vertically formed through the light emitting device array 1. Sweat from the skin 3 may be evaporated through a through hole 80. The heat from the light emitting device array 1 may be radiated through the through hole 80. The sweat may be evaporated by taking heat from the light emitting device. As the sweat is not accumulated, the light emitting device array 1 may be prevented from being separated from the skin 3 and stronger adhesive force may be ensured.

The substrate may have a specific pattern processed thereon. In this case, the pattern may be formed by repeating the minimum unit of an area in which one light emitting device is placed. The minimum unit of forming the pattern may be defined as a cell. The concepts of the pattern and the cell may be similarly applied to at least one of the heat sink 20, the insulating layer 40, the connector 50, the fixing member 60, or the adhesive layer 70.

Figure 3:
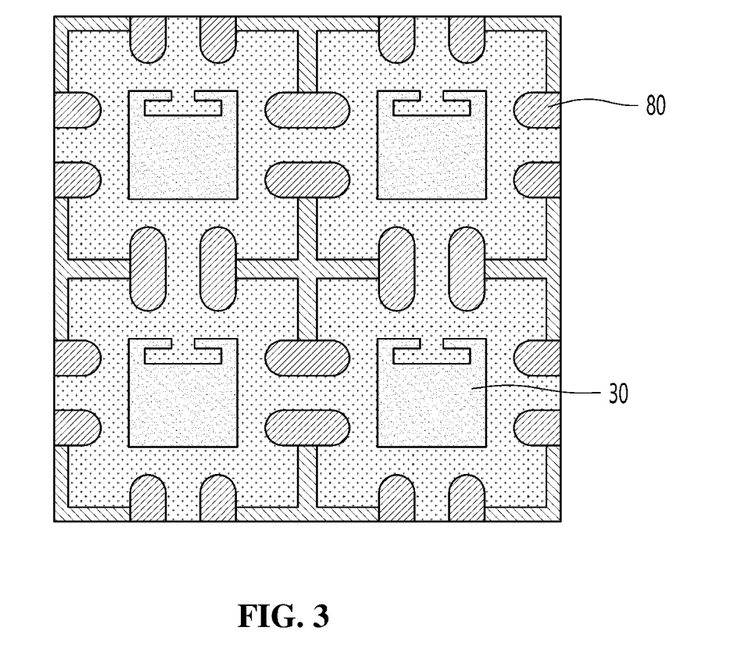
FIG. 3 is a plan view illustrating the light emitting device array.

FIG. 3 is a plan view illustrating the light emitting device array.

Referring to FIG. 3, two through holes 80 may be provided in a place to link cells to each other. The through hole 80 may be provided in the form of an elongated hole, and may extend in a direction to link the cells to each other. The through hole 80 may be provided in all components other than the light emitting device 30 and the fixing member 60. Through holes of each member may be aligned with each other. The through hole may be provided even in the fixing member 60. As long as the through hole has a shape of linking the light emitting device 30, the through hole may be provided in the light emitting device 30. The through hole may be empty therein. External air may be introduced into the through hole or withdrawn from the through hole.

Figure 4:
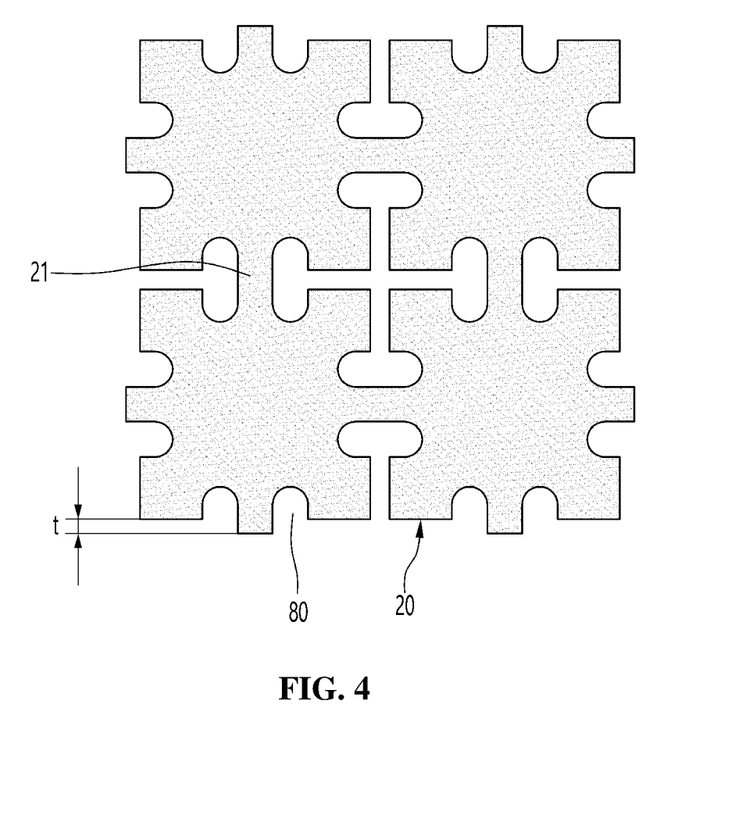
FIG. 4 is a plan view illustrating a heat sink.
Figure 5:
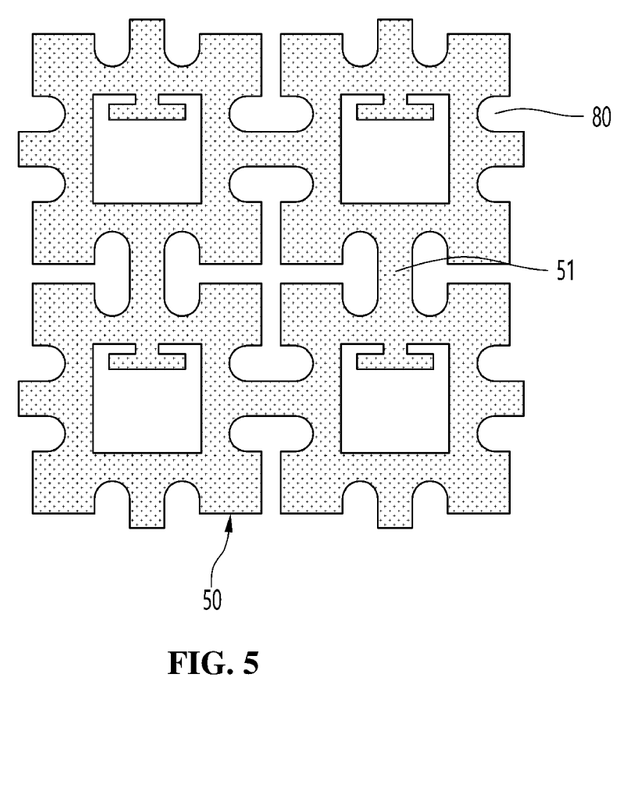
FIG. 5 is a plan view of a connector.

FIG. 4 is a plan view of the heat sink, and FIG. 5 is a plan view of the connector.

Referring to FIGS. 4 and 5, at least one of the heat sink 20 and the connector 50 may serve as interconnectors 21 and 51 to connect adjacent cells to each other. The through hole 80 may be provided in at least one of opposite side surfaces of the interconnector, preferably, two side surfaces of the interconnector. The interconnectors 21 and 51 may further protrude by the value of "t" from a side constituting each cell of the heat sink 20 and the connector 50. The interconnector is a part to link adjacent cells to each other. The interconnector may have a length greater than a thickness thereof. In other words, in the interconnector, a length extending in a longitudinal direction to link adjacent cells to each other may be greater than a length extending in a thickness direction perpendicular to the longitudinal direction. Accordingly, when adjacent cells are bent, the interconnector may be smoothly bent. The interconnector may prevent deformation from being concentrated.

The infrared light emitted from the light emitting device 30 may emit light upward when viewed from FIG. 2, pass through the adhesive layer 70 and the skin, and reach the electronic device 4.

Hereinafter, a method for fabricating a light emitting device array according to an embodiment will be described.

Figure 6A:
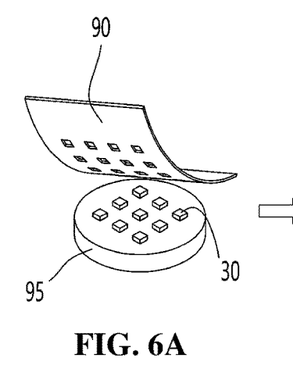
FIGS. 6A to 6C are views illustrating a procedure of providing at least two light emitting devices.
Figure 6B:
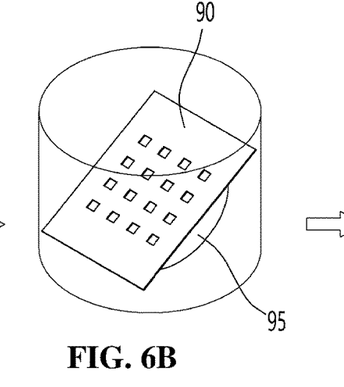
Figure 6C:
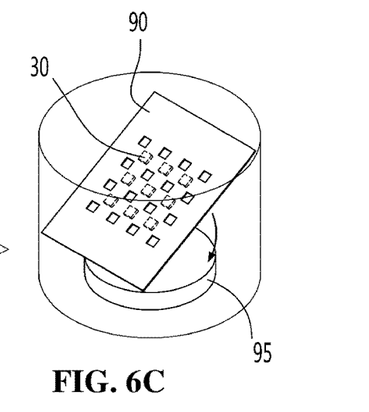
Figure 7:
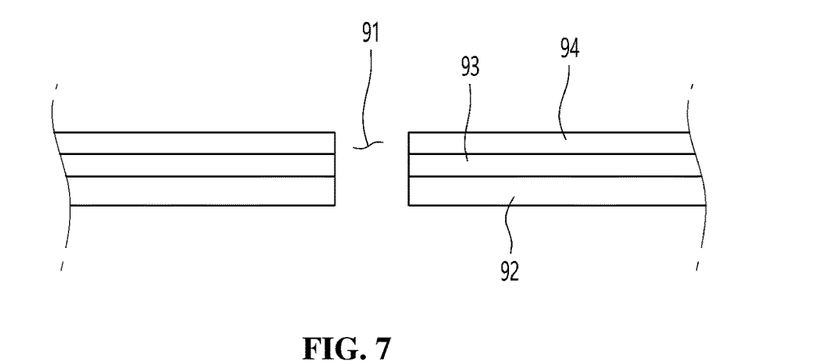
FIG. 7 is a cross-sectional view of a stamping substrate.

FIGS. 6A to 6B are views illustrating the procedure of providing at least two light emitting devices, FIG. 6A is a view illustrating that a stamping substrate 90 is attached to the light emitting device 30, and FIGS. 6B and 6C are views illustrating that the light emitting device 30 is separated from a sacrificial substrate 95 through an isotropic etching process and an undercut process. FIG. 7 is a cross-sectional view of the stamping substrate.

Referring to FIGS. 6A and 7, the light emitting device 30 may be provided on the sacrificial substrate 95. The sacrificial substrate may use a GaAs substrate.

The light emitting device may be fabricated on the sacrificial substrate through epitaxial growth on the sacrificial substrate. An area in which the light emitting device is provided may be protected by a protective member. In this case, the protective member may be provided by sequentially performing a coating process, a baking process, a rehydration process, an ultra-light irradiation process, and a developing process with respect to photoresist.

The light emitting device protected by the protective member may be stamped through the stamping substrate 90. Referring to FIG. 7, the stamping substrate 90 may include a PI substrate 92 having the thickness of 25 µm, a Ti adhesive layer 93 having the thickness of 10 nm, and a PDMS 94 formed on the adhesive layer and having the thickness of 10 µm. The PDMS 94 may make contact with the light emitting device.

An etch hole 91 may be provided in the stamping substrate 90 such that an etchant flows into the sacrificial substrate.

Referring back to FIG. 6A, the stamping substrate 90 and the light emitting device 30 (in this case, the light emitting device is covered by the protective member) may be strongly attached to each other by pressing each other under a heating condition.

Referring to FIGS. 6B and 6C, the etchant may flow into the etch hole 91 to etch the interface between the light emitting device 30 and the sacrificial substrate 95 to separate the sacrificial substrate.

A bottom electrode may be formed on a rear surface of the light emitting device through electron beam evaporation. The top electrode may be provided to the light emitting device before the protective member is stacked.

The light emitting device may be transferred to the stamping substrate through the above procedure. The yield rate of the light emitting device array may be improved through the above procedure.

FIGS. 8A to 8H are views illustrating a procedure of fabricating a light emitting device array.

Figure 8A:
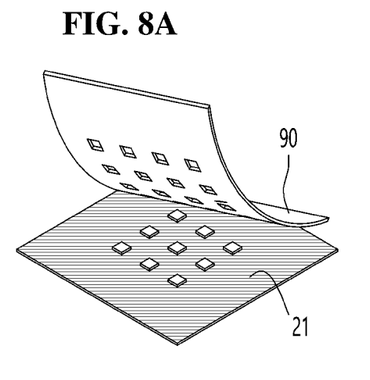
FIGS. 8A to 8H are views illustrating a procedure of fabricating a light emitting device array.
Figure 8B:
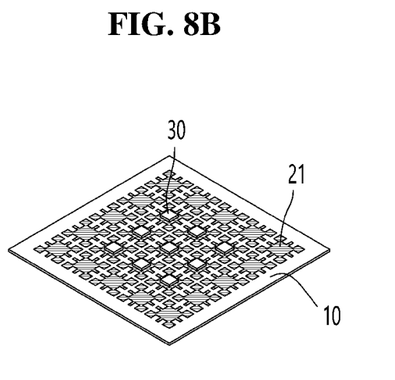

Referring to FIG. 8B, a bottom member on which the heat sink layer is stacked on the substrate 10 is prepared. The stamping substrate 90 is pressed against the bottom member under heating conditions. The process conditions may be 95° C., 10 minutes, and a pressure of 1.4 Mpa. This will be called "cold welding". According to the above process, the first electrode of the light emitting device may make contact with the heat sink.

The protective member may be removed with acetone. The stamping substrate is separated and removed from the light emitting device. Through this process, the transfer action of the stamping substrate may be terminated.

Referring to FIG. 8B, the heat sink layer may be processed to have a specific pattern in the present process. The heat sink layer may be processed through photoresisting, masking, and etching processes.

Figure 8C:
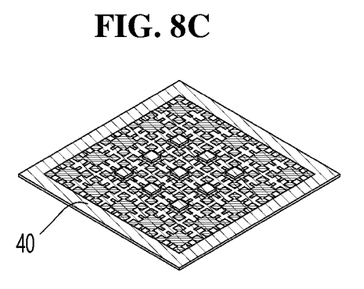

Referring to FIG. 8C, the insulating layer 40 may be provided through a spin casting process. A via hole may be formed in the insulating layer to expose the electrode of the light emitting device.

Figure 8D:
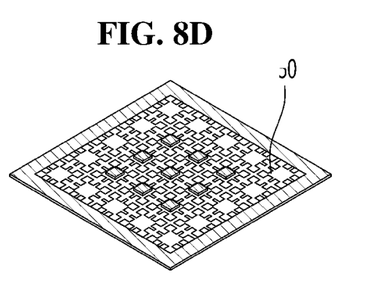

Referring to FIG. 8D, a connector layer may be provided by sputtering nickel and gold.

Figure 8E:
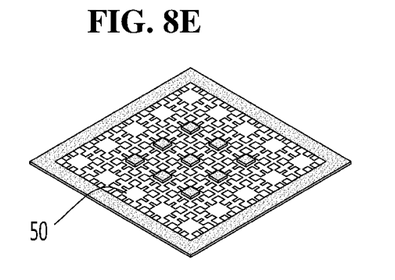

Referring to FIG. 8E, the connector 50 may be provided by processing the connector layer through a dry etching (RIE) scheme.

Figure 8F:
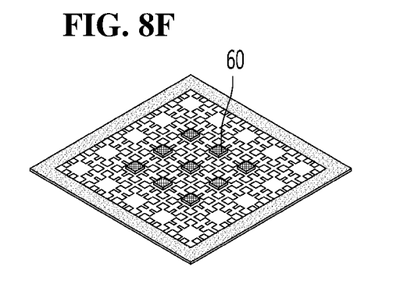

Referring to FIG. 8F, the fixing member 60 corresponding to the light emitting device 30 may be cured through spin-casting and an ultraviolet ray curing processes.

Figure 8G:
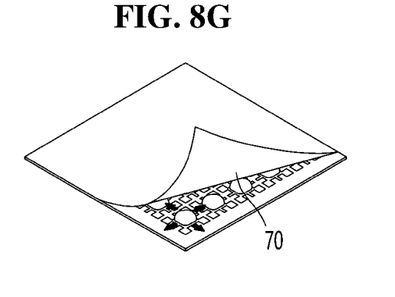
Figure 8H:
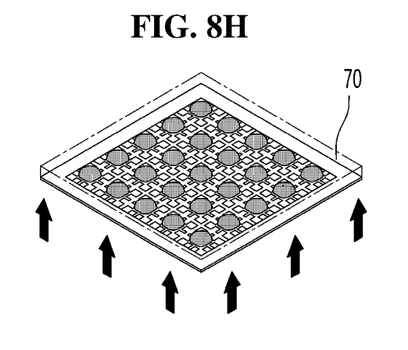

Referring to FIGS. 8G and 8H, to provide the adhesive layer, an adhesive material may be screen-printed (see FIG. 8G), and then cooling air may be injected from the bottom to the top (see FIG. 8H). The adhesive material is Silbione RT Gel 4717 A/B or Bluestar Silicone, as described above.

The spin-casting scheme is not employed to provide the adhesive layer, because the through hole may be clogged.

The light emitting device array may be provided through the process.

Figure 9A:
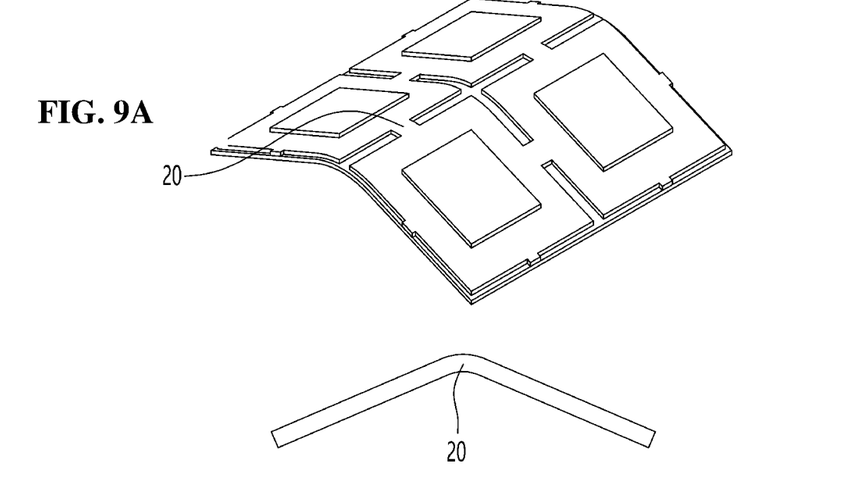
FIGS. 9A and 9B are views illustrating an operation of an interconnector.
Figure 9B:
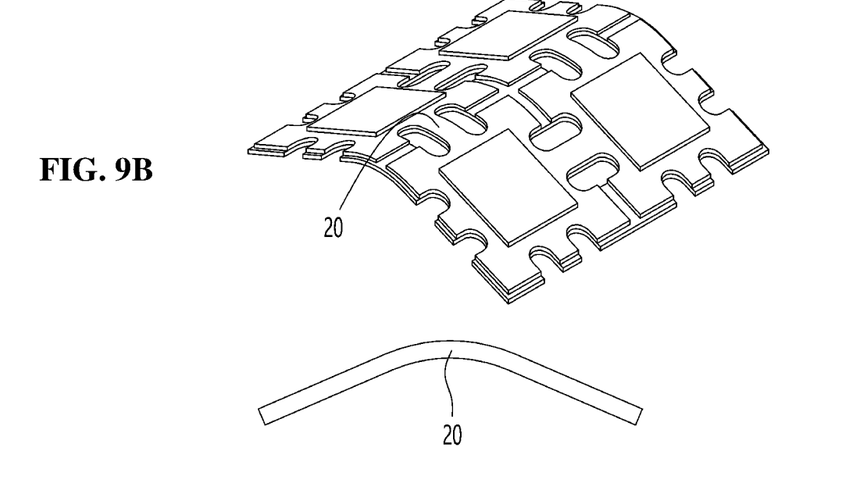

FIGS. 9A and 9B are views illustrating the action of the interconnector, FIG. 9A illustrates a comparative example, and FIG. 9B illustrates an embodiment.

Referring to FIGS. 9A and 9B, deformation of the interconnector 20 may be reduced by forming an interconnector 20 which is thin and long.

FIG. 10 is a view illustrating the arrangement of the light emitting device with respect to the heat sink.

Figure 10A:
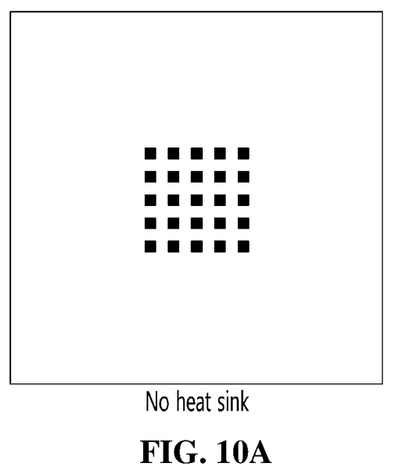
FIGS. 10A to 10D are views illustrating the arrangement of the light emitting device with respect to the heat sink.
Figure 10B:
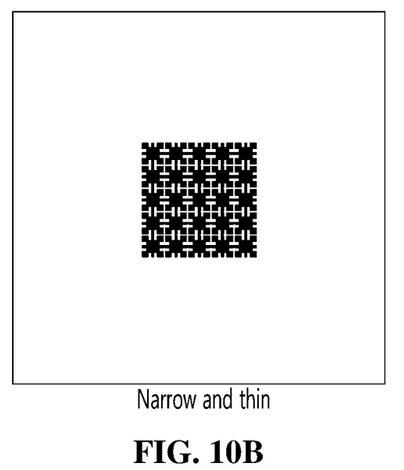
Figure 10C:
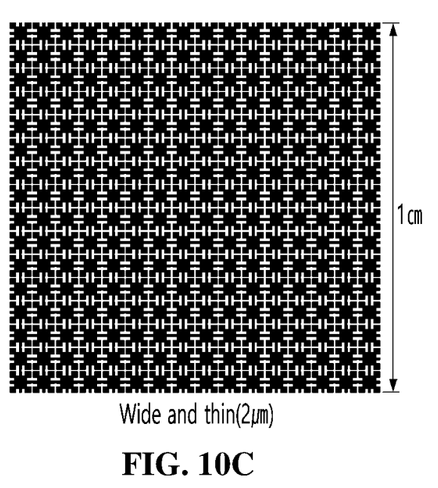
Figure 10D:
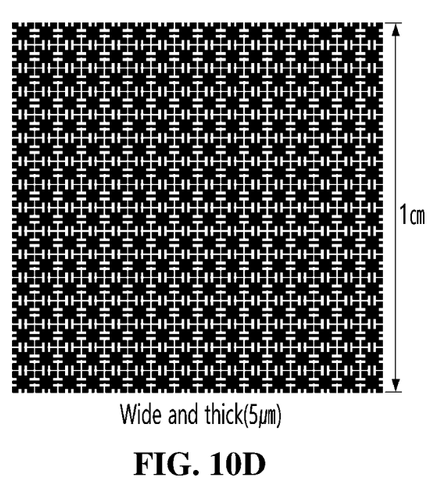

FIG. 10A illustrates the case that the heat sink is not disposed, FIG. 10B illustrates the case that the heat sink is disposed only in the area of the light emitting device, FIG. 10C illustrates that the heat sink having the thickness of 2 µm is widely disposed even in an area having no light emitting device, and FIG. 10D is a view illustrating that the heat sink having the thickness of 5 µm is disposed in the area having no light emitting device.

The experimental results for the cases are illustrated in FIGS. 11A to 11D. FIG. 10A illustrates the case of "no heat sink", FIG. 10B illustrates the case of "narrow and thin", FIG. 10C illustrates the case of "wide and thin", and FIG. 10D illustrates the case of "wide and thick".

Figure 11A:
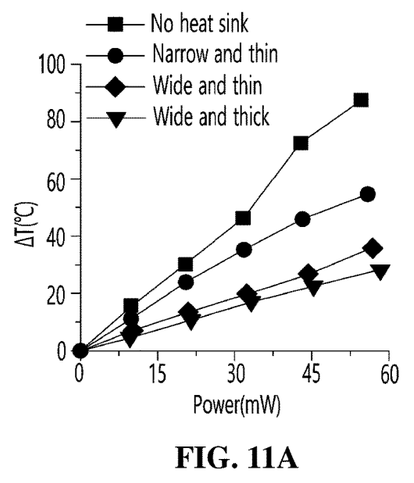
FIGS. 11A to 11D are views illustrating an experimental result of each case of FIGS. 10A to 10D.

Referring to FIG. 11A, when the heat sink is provided to be wider than the area in which the light emitting device is disposed, the temperature increase is less than those of other cases. In addition, when there is no heat sink, the temperature is increased to the extent that a user becomes scalded. Accordingly, it is preferred that the heat sink is disposed in a space wider than an area in which the light emitting device is disposed.

Figure 11B:
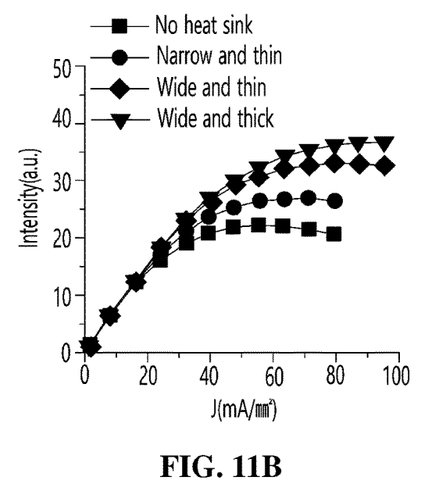
Figure 11C:
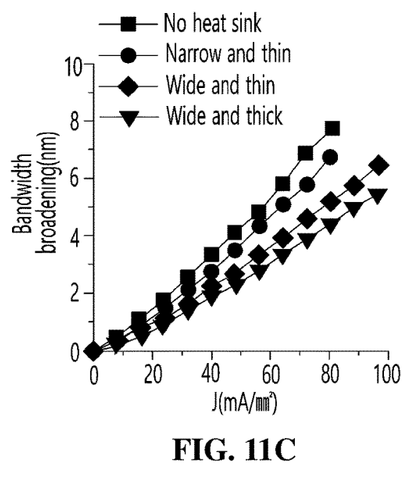

FIGS. 11B and 11C illustrate experimental results for light intensity and full width at half maximum (FWHM), respectively. Referring to FIGS. 11B and 11C, it is more preferred that the heat sink is provided with a thicker thickness in wider area.

Figure 11D:
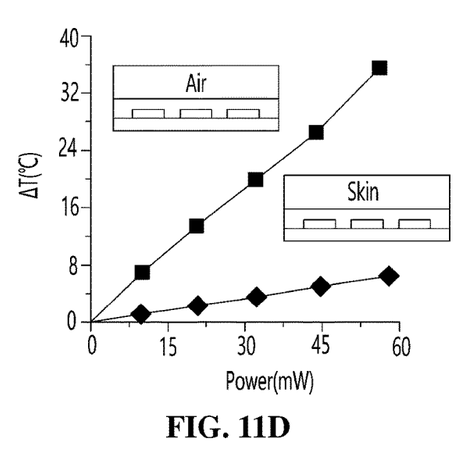

FIG. 11D is a view illustrating the comparison between the model of FIG. 10D exposed to air and the model of FIG. 10D making contact with the skin. When two curves are compared with each other, it may be understood that the model of FIG. 10D making contact with the skin represents a lower temperature increase as conduction heat is more transferred.

According to the present disclosure, there may be provided the light emitting device array capable of transmitting energy to the electronic device implantable into a living body.

What is claimed is:

1. A light emitting device array comprising:
   a substrate;
   a heat sink disposed on the substrate;
   at least two light emitting devices disposed on the heat sink and spaced apart from each other;
   a connector disposed on the light emitting device and configured to apply power;
   an insulating layer interposed between the heat sink and the connector;
   a fixing member configured to support a position of the light emitting device, on the light emitting device; and
   an adhesive layer provided on the fixing member to make contact with a skin.

2. The light emitting device array of claim 1, further comprising:
   a through hole vertically formed through the light emitting device array and having an inner part that is empty.

3. The light emitting device array of claim 1, further comprising:
   through holes formed at least two of the substrate, the heat sink, the connector, the insulating layer, or the adhesive layer.

4. The light emitting device array of claim 3, wherein the through holes are vertically aligned.

5. The light emitting device array of claim 3, wherein the through holes are provided in all the substrate, the heat sink, the connector, the insulating layer, and the adhesive layer.

6. The light emitting device array of claim 1, wherein the heat sink includes a multi-metal layers, and a lowermost part of the multi-metal layers includes copper (Cu).

7. The light emitting device array of claim 1, wherein the heat sink and the light emitting device directly make contact with each other.

8. The light emitting device array of claim 1, wherein the heat sink receives power applied, and
   wherein the light emitting device receives power applied through the connector and the heat sink.

9. The light emitting device array of claim 1, wherein at least one of the heat sink and the connector has a pattern formed by repeating a cell serving as an area in which one light emitting device is disposed, and
   wherein at least one of the heat sink and the connector has an interconnector to connect a pair of cells adjacent to each other.

10. The light emitting device array of claim 9, wherein a through hole is provided in at least one of opposite side surfaces of the interconnector to allow air to flow through the through hole.

11. The light emitting device array of claim 9, wherein the interconnector protrudes from each side of the cell.

12. The light emitting device array of claim 9, wherein the interconnector has a length that extends in a longitudinal direction to link adjacent cells to each other, and is greater than a length extending in a thickness direction perpendicular to the longitudinal direction.

13. A charging system for an electronic device implantable into a living body, the charging system comprising:
   a living-body implantable electronic device inserted into a skin and having a secondary battery; and
   a light emitting array configured to make contact with the skin,
   wherein the light emitting array includes:
   a heat sink;
   at least two light emitting devices disposed on the heat sink and spaced apart from each other;
   a connector disposed on the light emitting device;
   an insulating layer disposed on an interface between the heat sink and the connector; and
   an adhesive layer provided on the connector to make contact with the skin.

14. The charging system of claim 13, further comprising:
   a through hole vertically formed through the light emitting device array and having an inner part that is empty.

15. The charging system of claim 13, wherein at least one of the heat sink and the connector apply power to the light emitting device.

* * * * *